United States Patent [19]
Kuehn et al.

[11] Patent Number: 5,288,231
[45] Date of Patent: Feb. 22, 1994

[54] LIGHT SHIELD FOR DENTAL APPARATUS

[75] Inventors: Paul Kuehn, Eau Claire, Wis.; Thomas A. Lansing, Pine Springs, Minn.

[73] Assignee: Pinnacle Products, Inc., St. Paul, Minn.

[21] Appl. No.: 27,785

[22] Filed: Mar. 8, 1993

[51] Int. Cl.$^5$ .............................................. A61C 1/00
[52] U.S. Cl. ..................................... 433/29; 433/229; 359/361; 250/515.1
[58] Field of Search ................ 433/29, 229, 215; 250/515.1, 519.1; 359/361

[56] References Cited

U.S. PATENT DOCUMENTS

| | | | |
|---|---|---|---|
| 2,085,627 | 6/1937 | Bodnar | 250/504 |
| 2,705,290 | 3/1955 | Newman | 250/504 |
| 4,445,858 | 5/1984 | Johnson | 433/141 |
| 4,522,594 | 6/1985 | Stark et al. | 433/141 |
| 4,640,685 | 2/1987 | Croll | 433/141 |
| 4,662,842 | 5/1987 | Croll | 433/141 |
| 4,822,278 | 4/1989 | Oliva et al. | 433/91 |
| 4,900,253 | 2/1990 | Landis | 433/30 |
| 5,017,140 | 5/1991 | Ascher | 433/215 |

OTHER PUBLICATIONS

Technical Information on K-RESIN Polymers, date of first publication unknown, but prior to 1992.
Product Information, Styron General Purpose Polystyrene Resins, Dow Chemical Company, 1981.
Ebb A. Berry III, et al., "An Evaluation of Lenses Designed to Block Light Emitted by Light-Curing Units," JADA, vol. 112, Jan. 1986, pp. 70-72.
"The Effects of Blue Light on the Retina and the Use of Protective Filtering Glasses," JADA, vol. 112, Apr. 1986, pp. 533-535.
P. L. Fan, et al., "Evaluation of Light Transmission Characteristics of Protective Eyeglasses for Visible Light-Curing Units," JADA, vol. 113, Nov. 1986, pp. 770-772.
Brochure entitled "The Eye Protection System," by EFOS, Inc., date of first publication unknown but prior to 1992.

*Primary Examiner*—Cary E. O'Connor
*Attorney, Agent, or Firm*—Foley & Lardner

[57] ABSTRACT

A light shield is provided for dental apparatus which shines light onto light curable material used to repair teeth. The shield is formed of a plastic material which substantially attenuates light in the blue range, and can be mounted onto the guide tube of the light gun utilizing engagement members defined between slits cut in the plastic sheet forming the body of the shield. The engagement members between the slits are displaced as the light shield is pressed onto the tip of the guide tube, with the engagement members then resiliently pressing against the periphery of the guide tube to firmly hold the shield in place. The shield can be easily removed by the dentist after the procedure with the patient is completed, and is economical so that it may be disposed of after one use.

7 Claims, 1 Drawing Sheet

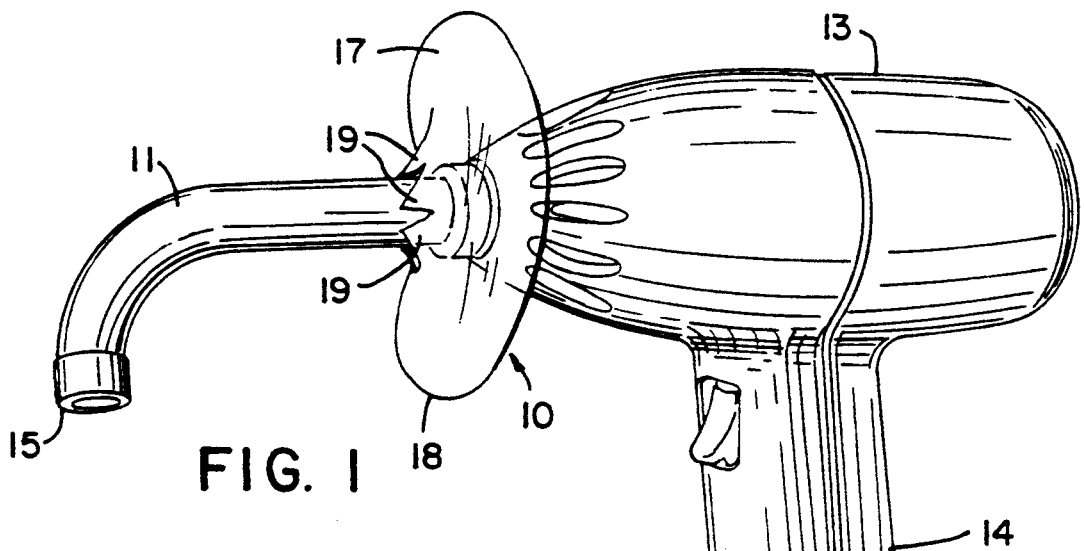
FIG. 1
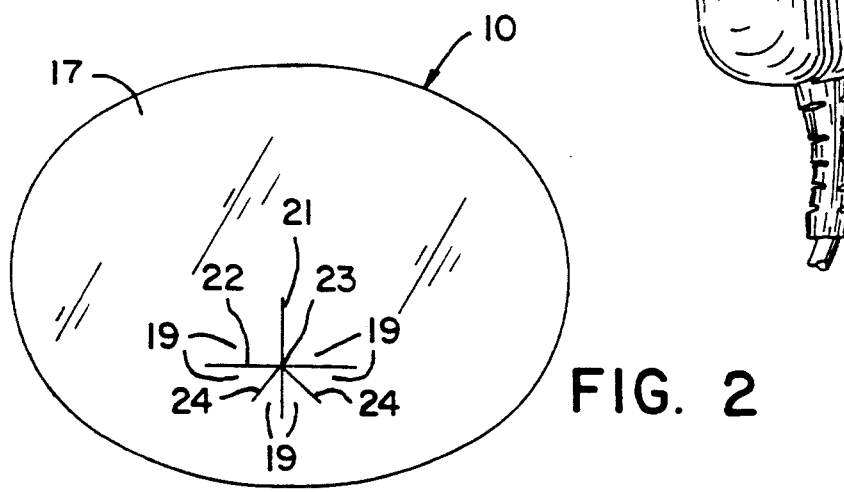
FIG. 2
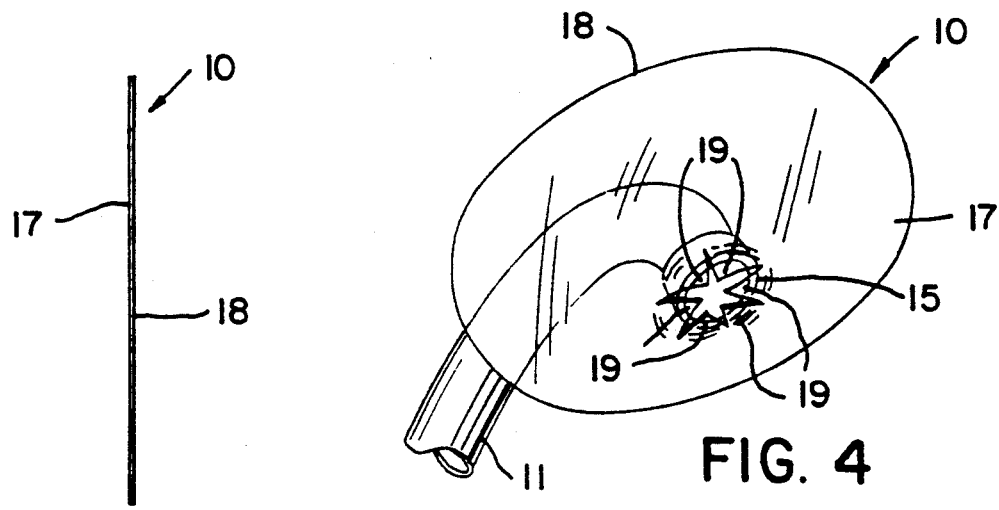
FIG. 3
FIG. 4

LIGHT SHIELD FOR DENTAL APPARATUS

FIELD OF THE INVENTION

This invention pertains generally to the field of dental apparatus and particularly to shields for use with dental equipment which uses light to cure dental resins.

BACKGROUND OF THE INVENTION

In modern dentistry, materials are used in the repair of teeth which require the application of light, particularly blue light, and sometimes near ultraviolet light, to cure the material. Typically, a dentist uses a hand held light gun with a guide tube to direct the light to the area of the patient's teeth to which the light curable material has been applied. Common dental visible light activated resin systems are polymerized by blue light in the 470 nm range. To obtain proper curing, it is necessary that the light be applied to the material for a significant period of time, e.g., 30 seconds or more. To ensure that the light from the light gun is applied to the proper area, the dentist or hygienist generally must observe where the light is being applied during this time.

Prolonged or repeated exposure to ultraviolet or blue light can lead to cataracts. Overexposure to relatively short wavelength visible light (e.g., less than 500 nm) may contribute to premature aging of the cornea and to senile macular degeneration. To avoid potential eye problems, dentists and hygienists commonly use light filters attached to their glasses which filter out the shorter wavelengths, or various types of light shields which are available as attachments to the light gun or which may be held separately from the light gun.

Because of the increasing concerns with possible cross contamination between patients, dental equipment that is in contact with or proximate to a patient generally must be sterilized before it is used again with another patient or disposed of altogether. Light shields presently available which attach to the light gun are generally relatively expensive, and it is not economically feasible to dispose of these shields after use with one patient. Existing disposable light shields have typically not been as effective as the more permanent type of shields and not as convenient to use. In particular, disposable shields often are not easily placed on the light gun before use and easily removed after use by the dentist, especially where surgical gloves are used by the dentist or hygienist.

SUMMARY OF THE INVENTION

In accordance with the present invention, a light shield is provided which is simple, easy to use, inexpensive so that it can be economically disposed of after one use, stable once in place on the guide tube of a light gun, and effective to protect the dentist's eyes from excessive exposure to potentially damaging wavelengths of light. The shield comprises a rounded, preferably oval sheet of crystalline styrene plastic which filters out a substantial portion, e.g., 97% or more, of the blue light (e.g., shorter than 500 nm) incident on the shield, and yet is substantially transparent to wavelengths longer than the blue or near ultraviolet wavelengths being filtered. In a preferred material, light in the wavelengths of 560 nanometers or less is substantially filtered.

The shield is provided with slits that define resilient engagement members between them to provide a firm but adjustable mounting of the shield on the guide tube of a light gun. The engagement members are defined between the slits and, because of the resiliency of the plastic of the shield, will bend resiliently as the guide tube is inserted into the center intersecting point of the slits. The length of the slits is selected with respect to the standard diameter of the guide tube for typical light guns so that the guide tube fills a substantial portion but less than all of the radial area defined between the ends of the slits, so that the engagement members are deformed to press against the sides of the guide tube and hold the shield firmly in place on the guide tube without substantial distortion of the shape of the shield. The shield can be readily adjusted in position by the dentist by grasping the shield and sliding or rotating it with respect to the guide tube. The pattern of slits is preferably selected such that a cluster of shorter slits converges on the central point of the opening and is opposed by longer, more widely separated slits, which define wider engagement members than those defined between the shorter slits. Such a pattern of slits serves to more readily center the shield in position on the guide tube.

Attachment of the shield to the guide tube is readily accomplished by simply pressing the end of the guide tube against the engagement members to press the guide tube through the hole defined by the deflected engagement members. When the procedure on the patient is completed, the shield is similarly easily removed by the dentist by simply holding the shield between the dentist's fingers and pulling it off the guide tube.

The shield itself can be die cut from a sheet of plastic filter material. Moreover, the slits defining the engagement members can be readily die cut at the same time as the periphery of the shield, resulting in a simple, inexpensive, and precise forming operation for the shield. In this manner, the shield can be formed inexpensively so that it is economically disposable after use with a single patient.

Further objects, features and advantages of the invention will be apparent from the following detailed description when taken in conjunction with the accompanying drawings.

BRIEF DESCRIPTION OF THE DRAWINGS

In the drawings:

FIG. 1 is an illustrative perspective view of a light shield in accordance with the present invention shown in place on the guide tube of a light gun.

FIG. 2 is a plan view of the light shield of the present invention.

FIG. 3 is a side view of the light shield of FIG. 2.

FIG. 4 is an illustrative view showing the mounting of the light shield of the invention onto the tip of the guide tube of a light gun.

DETAILED DESCRIPTION OF THE INVENTION

With reference to the drawings, wherein like numerals refer to like parts, the light shield of the present invention is shown generally at 10 in FIG. 1 mounted on the guide tube 11 of a light gun 13. The light gun 13 has a handle 14 by which the dentist holds the light gun with the tip 15 of the guide tube 11 adjacent to the teeth of the patient at the position at which the material to be cured is located. The light gun 13 is held by the dentist so that the shield 10 is interposed in his or her line of sight leading to the position at which light from the tip 15 of the guide tube is applied to the teeth.

As illustrated in FIGS. 1 and 2, the light shield 10 has a sheet-like plastic body 17 with a rounded outer periphery 18. Resilient engagement members 19 are integrally formed in the plastic body 17 to engage against the outside of the tube 11 to hold the shield 10 in place on the tube.

As shown in FIG. 2, the engagement members 19 are preferably defined between a "vertical" slit 21 and a "horizontal slit" 22 which are perpendicular and intersect at a central point 23, and two shorter slits 24 which extend away from the central point 23 at approximately a 45° angle to the slits 21 and 22. Thus, it is seen that in the preferred engagement structure of FIG. 2, two engagement members 19 are formed above the horizontal slit line 22, while four engagement members, each being smaller than the engagement members defined between the slits 21 and 22, are defined between the slit 22 and the slits 24, and between the portion of the slit 21 below the horizontal slit 22 and the adjacent shorter slits 24.

As illustrated in FIG. 4, to emplace the shield 10 on the guide tube 11, the dentist holds the shield so that the tip 15 of the guide tube is pressed against the engagement members 19, and presses the tip 15 through the opening formed as the engagement members are pushed out of the way by the tip 15. The engagement members 19 then bend as shown in FIG. 1 to resiliently hold the shield 10 in place on the guide tube with the shield extending out generally perpendicularly to the guide tube. The dentist can easily adjust the position of the shield 10 on the guide tube by sliding it toward or away from the tip and by rotating it about the guide tube. When the procedure on the patient is completed, the dentist pulls the light shield off the guide tube and disposes of the shield.

A preferred material for the body 17 of the shield is a crystalline styrene plastic with coloring material therein effective to filter out light in the blue and near ultraviolet range, and preferably to substantially filter out (97% or more) light wavelengths shorter than 560 nanometers. A suitable resin from which the film can be extruded is available under the name KRO4 K-Resin from Phillips Chemical Company, or Styron resin from Dow Chemical, with FDA approved coloring agents mixed therein (typically orange coloring) available from various suppliers (e.g., Spectrum Colors, Inc.), and such material in a thickness of 0.008 inch (8 mils) has been found satisfactory for the purposes of the present invention. A styrene material in this thickness can be readily die cut to cut the slits 21, 22 and 24 to define the engagement members 19, and to define the outer periphery 18 of the shield. This material in this thickness also allows the engagement members 19 to resiliently deflect as they are engaged by the tip of the guide tube 15 to allow the guide tube to pass through the opening defined as these engagement members are deflected, allowing the engagement members to resiliently press against the surface of the guide tube to hold the shield in place.

The light shield has a preferred shape as shown in FIG. 2, being substantially oval (elliptical) with the central point 23 of the slits located along the narrower central axis of the elliptical periphery 18 and off of the long axis of the ellipse. For example, the central point 23 may preferably be formed halfway between the long axis of the ellipse and the edge. Locating the engagement members at this position enables mounting of the light shield 10 on the tube at a position such that a relatively wide area of the shield is provided between the guide tube and the shield periphery 18 through which the dentist can observe the area of the teeth being treated with light. By placing the engagement members 19 close to but spaced away from the periphery, the plastic material of the shield is strong enough to prevent the pressure from the guide tube, as it deflects the engagement members 19, from tearing through the plastic. One advantage of utilizing shorter slits 24 at the lower portion of the opening, to define smaller engagement members 19 below the horizontal slit 22, is that less pressure is applied on these smaller engagement members as the guide tube is pressed against them than is applied against the larger engagement members 19 above the horizontal slit 22, thereby making it less likely that the plastic adjacent to the slits below the horizontal slit 22 would be torn as the shield is pressed onto the guide tube.

In an exemplary preferred form, the shield periphery is an ellipse with a long axis of 3.0 inches and a short axis of 2.25 inches. The vertical slit 21 is preferably 0.669 inch long, lying along the short axis of the ellipse, and the horizontal slit 22 is preferably 0.866 inch long and spaced 0.591 inch from the closest point of the periphery 18. The length of the portion of the slit 21 below the horizontal slit 22 is preferably 0.276 inch, and terminates 0.315 inch from the nearest point of the periphery. The short slits 24 are also preferably 0.276 inch long, and extend at 45° angles with respect to the slits 21 and 22.

The shield of the present invention can be formed in an inexpensive manner by die cutting the shield from a commercially available base sheet of the material to form the body 17 of the shield. In a preferred process, a die is provided having a knife edge which cuts into the plastic base sheet to define the periphery 18 of the shield, and also has knife edges which simultaneously cut the slits 21, 22 and 24. Because the slits 21, 22 and 24 converge on a central point 23 in the preferred pattern, no material need be removed from the body 17 of the shield to define the opening in the shield into which the tube 11 may be inserted, thereby simplifying the manufacturing process and allowing the shield to be produced in the simplest and most economical manner.

It is understood that variations of the shield of the invention may be utilized without departing from the scope of the present invention. For example, the outer periphery 18 of the shield may be formed as a circle, or any other geometric form, although the oval shape as shown in FIG. 2 is preferred. Further, if desired, the engagement members which define the opening in the shield may be formed such that they do not meet at a central point 23 as illustrated in FIG. 2, but have a portion of the shield body removed so that a central opening may be formed between the ends of the engagement members 19. As noted above, this is not preferred since it results in an extra step in the manufacturing process.

It is understood that the invention is not confined to the particular construction and arrangement of parts herein illustrated and described, but embraces such modified forms thereof has come within the scope of the following claims.

What is claimed is:

1. A light shield for mounting on the guidetube of a dental light gun which provides light for curing dental materials, comprising:

a body formed of a sheet of resilient plastic material, the body having an outer periphery, the body formed of a plastic material which substantially blocks light of wavelengths in the blue range and substantially passes longer wavelengths, and engagement members formed integrally with the body of the shield, the engagement members defined by slits in the body of the shield which converge toward an intersection to define the engagement members as flexible parts which may be deflected away from the central point as the tip of a guide tube of a light gun is pressed against the engagement members to mount the shield on the guide tube.

2. The light shield of claim 1 wherein the outer periphery of the shield is elliptical in shape and the central point to which the slits converge is formed at a position on the shorter axis of the ellipse away from the central point of the ellipse.

3. The light shield of claim 1 wherein the engagement members are defined between a set of slits which converge to and intersect at a central point, the slits including at least a vertical slit, a horizontal slit which intersects the vertical slit perpendicularly, and two slits which intersect the central point and which extend below the horizontal slit and are shorter than the horizontal and the vertical slit.

4. The light shield of claim 1 wherein the body of the light shield is formed of crystalline styrene plastic.

5. The light shield of claim 4 wherein the body of the light shield is approximately 0.008 inch thick.

6. The light shield of claim 1 wherein the body is formed to substantially attenuate light having wavelengths shorter than about 560 nanometers.

7. The light shield of claim 1 wherein the body of the light shield is formed of orange colored plastic.

* * * * *